(12) United States Patent
Zhou

(10) Patent No.: US 10,368,704 B2
(45) Date of Patent: Aug. 6, 2019

(54) SMART TOILET WITH FUNCTION OF ELECTROCARDIOGRAPHIC LEAD MONITORING

(71) Applicant: Zhongshan Anbo Health Technology Co., Ltd., Zhongshan (CN)

(72) Inventor: Wenhui Zhou, Zhongshan (CN)

(73) Assignee: ZHONGSHAN ANBO HEALTH TECHNOLOGY CO., LTD., Zhongshan (CN)

( * ) Notice: Subject to any disclaimer, the term of this patent is extended or adjusted under 35 U.S.C. 154(b) by 0 days.

(21) Appl. No.: 15/916,288

(22) Filed: Mar. 9, 2018

(65) Prior Publication Data

US 2018/0271340 A1 Sep. 27, 2018

(30) Foreign Application Priority Data

Mar. 24, 2017 (CN) .......................... 2017 1 0182243

(51) Int. Cl.
*A61B 5/00* (2006.01)
*A61B 5/0402* (2006.01)
*A47K 13/24* (2006.01)
*A47K 17/02* (2006.01)

(52) U.S. Cl.
CPC ............ *A47K 13/24* (2013.01); *A61B 5/0402* (2013.01); *A61B 5/6891* (2013.01); *A47K 17/02* (2013.01)

(58) Field of Classification Search
CPC .... A47K 13/24; A61B 5/6894; A61B 5/1455; A61B 5/6891
See application file for complete search history.

(56) References Cited

U.S. PATENT DOCUMENTS

| 9,828,755 | B1* | 11/2017 | Clements | .................. E03D 9/08 |
| 2003/0233034 | A1* | 12/2003 | Varri | .................... A61B 5/1102 |
| | | | | 600/301 |
| 2018/0020984 | A1* | 1/2018 | Hall | ..................... A61B 5/0059 |
| | | | | 600/301 |

* cited by examiner

*Primary Examiner* — Janie M Loeppke
(74) *Attorney, Agent, or Firm* — Gokalp Bayramoglu

(57) ABSTRACT

A smart toilet with a function of electrocardiographic lead monitoring, includes a toilet base, and further includes a body connected to the toilet base. The body is provided with a controller, and an electrocardiographic lead monitoring module, a display or voice prompt module, a power supply module for supplying power, which are electrically connected to the controller respectively. The human body ECG signal obtained by the electrocardiographic lead monitoring module is processed by the controller, to obtain human body electrocardiographic lead data, and the display or voice prompt module is controlled to output the data. The invention combines the electrocardiographic monitoring function with the toilet, which enables people to know electrocardiographic data quickly and conveniently while using the toilet, so as to understand their own heart health, thereby detecting and dealing with possible diseases as soon as possible.

14 Claims, 3 Drawing Sheets

SMART TOILET WITH FUNCTION OF ELECTROCARDIOGRAPHIC LEAD MONITORING

CROSS REFERENCE TO RELATED APPLICATIONS

This application is based upon and claims priority to Chinese Patent Application No. CN201710182243.5, filed on Mar. 24, 2017, the entire content of which is incorporated herein by reference.

TECHNICAL FIELD

The present invention relates to a toilet, particularly to a smart toilet with a function of electrocardiographic (ECG) lead monitoring.

BACKGROUND OF THE INVENTION

The main functions which existing smart toilets provide are heating-up of the toilet bases, cleaning with warm water, drying with warm air, and deodorization. However, overall, functions are limited, and the usage is invariant. It is hard to make a breakthrough. In recent years, with the increasing requirements of people for the quality of life, the demand for quality health is getting higher and higher. It is a trend that the personal health care functions are introduced into the smart toilet. However, some existing smart toilets cannot satisfy the requirements of people to understand their health conditions. In the modern society, the incidence of cardiovascular disease is getting higher and higher, and people with this disease are increasing day by day. Also, it is a trend that younger people are increasingly getting prone to this disease. For this reason, how to make people monitor their own heart health condition quickly and easily so that people can respond in time, becomes an important issue.

SUMMARY OF THE INVENTION

In order to solve the above-mentioned problems, the present invention provides a smart toilet with a function of electrocardiographic lead monitoring which enables people to monitor their own heart health condition quickly and easily while they are using the toilet, so as to detect and deal with possible diseases as soon as possible.

The technical solutions of the present invention are as follows.

A smart toilet with a function of electrocardiographic lead monitoring, including toilet base 2, wherein the smart toilet further includes body 1 connected to the toilet base. The body 1 is provided with controller 3 and electrocardiographic lead monitoring module 4, display or voice prompt module 5, power supply module 30 for supplying power, which are electrically connected to controller 3 respectively. Electrocardiographic lead monitoring module 4 further includes electrocardiographic lead monitoring probe 41 arranged on the body and electrical signal processing circuit 43 electrically connected to electrocardiographic lead monitoring probe 41. A human body ECG signal is obtained by electrocardiographic lead probe 41 and transmitted to the electrical signal processing circuit 43. A processed electrical signal is transmitted to the controller by electrical signal processing circuit 43. The processed electrical signal transmitted to the controller is further processed to obtain human body electrocardiographic lead data. Display or voice prompt module 5 is controlled by the controller to output the data.

Body 1 is further provided with key input module 6 that is electrically connected to controller 3 and is used to send user operation information back to controller 3.

Body 1 includes main body 10 and toilet seat 12, wherein the toilet seat is pivotally connected to main body 10, wherein after being rotated, the toilet seat covers toilet base 2.

Body 1 includes main body 10 and armrest 11 arranged on main body 10.

There are three electrocardiographic lead monitoring probes 41, respectively arranged on the toilet seat and the armrest, to receive ECG signals from the human legs and the human hands.

The smart toilet further includes human body sensing module 7 which is electrically connected to controller 3 and is used to sense whether the human body has sat down.

Human body sensing module 7 includes a capacitive sensor or a pressure sensor or an inductive electrode plate electrically connected to controller 3 and used to sense whether the user has sat down. The capacitive sensor, the pressure sensor, or the inductive electrode plate is arranged on toilet base 2 or body 1.

The smart toilet further includes toilet seat temperature control module 8 electrically connected to controller 3 and used to control temperature of the toilet seat. Toilet seat temperature control module 8 includes a first temperature sensor and a toilet seat heating module that are arranged on the toilet seat and electrically connected to the controller respectively.

The smart toilet further includes user cleaning module 9 electrically connected to controller 3. User cleaning module 9 includes water spraying module 90 configured to provide cleaning water, water pressure control module 91 configured to control an outlet water pressure of the cleaning water, water temperature control module 92 configured to control an outlet water temperature of the cleaning water, fan module 94 configured to provide drying air and air temperature control module 93 configured to control the temperature of the drying air. Water pressure control module 91, water temperature control module 92 and air temperature control module 93 are electrically connected to the controller.

Water spraying module 90 includes a nozzle for water outlet and a water pipe connecting the nozzle and an external water source. Water temperature control module 92 includes a second temperature sensor and a cleaning water heating module, which are arranged on the water pipe and electrically connected to controller 3 respectively. Water pressure control module 91 includes a proportional valve arranged between the nozzle and the water pipe and electrically connected to the controller. The air temperature control module includes a third temperature sensor and a drying air heating module, which are electrically connected to the controller respectively.

The smart toilet further includes communication module 31 electrically connected to the controller. Communication module 31 communicates with a smart device. The electrocardiographic lead data is transmitted to and displayed on the smart device through the communication module.

A control method for a smart toilet with a function of electrocardiographic lead monitoring, includes the following steps:

A: Power-on and initialization: initializing an initial state of each connection module through controller 3.

B: Performing power-on self-checking: performing a fault detection for each module through controller 3, if the self-checking is passed, proceeding to step C, otherwise, conducting an exception handling, displaying or reporting exception information through a display or voice prompt module 5.

C: Entering a main cycle and detecting whether user has sat down on the toilet by controller 3 through human body sensing module 7; if the user has sat down, electrocardiographic lead monitoring module 4 is started by controller 3; obtaining a human body ECG signal by the electrocardiographic lead monitoring module and transmitting the human body ECG signal to the controller; processing the electrical signal received by the controller to obtain electrocardiographic lead data of the human body; controlling display or voice prompt module 5 or communication module 31 communicating with the smart device to output the electrocardiographic lead data of the human body, then proceeding to step D; if no user has sat down, controlling electrocardiographic lead monitoring module 4 by controller to enter dormancy, and then proceeding to step D.

D: Detecting whether there is an input from key input module 6 by controller 3. If there is no input, returning to step C, otherwise proceeding to step E.

E: Performing corresponding operations according to the input at key input module 6 by controller 3: setting an outlet water temperature for the cleaning water, an outlet water pressure for the cleaning water and the drying air temperature, and starting user cleaning module 9 to provide the cleaning water or the drying air.

The smart toilet includes toilet base 2. The smart toilet further includes a body 1 connected to the toilet base. Body 1 is provided with controller 3 and electrocardiographic lead monitoring module 4, display or voice prompt module 5, and power supply module 30 for supplying power, which are electrically connected to controller 3 respectively. Electrocardiographic lead monitoring module 4 includes electrocardiographic lead monitoring probe 41 arranged on the body and electrical signal processing circuit 43 electrically connected to electrocardiographic lead monitoring probe 41. The human body ECG signal is obtained by electrocardiographic lead monitoring probe 41 and transmitted to electrical signal processing circuit 43. The processed electrical signal is transmitted to the controller by electrical signal processing circuit 43. The electrical signal received by the controller is processed to obtain the human body electrocardiographic lead data, and the display or voice prompt module 5 is controlled to output the data.

The smart toilet further includes human body sensing module 7 electrically connected to controller 3 to sense whether the human body has sat down.

The smart toilet further includes user cleaning module 9 electrically connected to controller 3. User cleaning module 9 includes water spraying module 90 for providing cleaning water, water pressure control module 91 for controlling an outlet pressure of the cleaning water, water temperature control module 92 for controlling the temperature of the cleaning water, fan module 94 for providing drying air and air temperature control module 93 for controlling the temperature of the drying air. Water pressure control module 91, water temperature control module 92 and air temperature control module 93 are electrically connected to the controller respectively.

Body 1 includes main body 10 and toilet seat 12, wherein the toilet seat is pivotally connected to main body 10, wherein after being rotated, the toilet seat covers toilet base 2. The smart toilet further includes toilet seat temperature control module 8 electrically connected to controller 3 and used to control the temperature of the toilet seat. Toilet seat temperature control module 8 includes a first temperature sensor and a toilet seat heating module which are arranged on the toilet seat and electrically connected to the controller respectively. The step E further includes performing corresponding operations according to the input at key input module 6 by the controller 3: setting the temperature of the toilet seat, and starting the toilet seat temperature control module to adjust the temperature of the toilet seat.

The step E further includes performing the corresponding operations according to the input at key input module 6 by controller 3: starting electrocardiographic lead monitoring module 4 by controller 3, obtaining an human body ECG signal by the electrocardiographic lead monitoring module; transmitting the human body ECG signal to the controller, processing the electrical signal received by the controller to obtain the human body electrocardiographic lead data, and controlling display or voice prompt module 5 or communication module 31 communicating with the smart device to output the human body electrocardiographic lead data.

Human body sensing module 7 includes a capacitive sensor, a pressure sensor, or an inductive electrode plate electrically connected to controller 3 and used to sense whether the user has sat down. The capacitive sensor, the pressure sensor, or the inductive electrode plate is arranged on toilet base 2 or the body 1.

Compared with the prior art, the present invention has the following advantages.

1. According to the present invention, a smart toilet with a function of electrocardiographic lead monitoring includes a toilet base and a body connected to the toilet base. The body is provided with a controller and an electrocardiographic lead monitoring module, a display or voice prompt module, and a power supply module for supplying power, and the electrocardiographic lead monitoring module, the display or voice prompt module, and the power supply module are electrically connected to the controller, respectively. The smart toilet of the present invention can obtain the human body ECG data through the electrocardiographic lead monitoring module and output the data through the display or voice prompt module. According to the present invention, the electrocardiographic lead monitoring function is combined with the toilet, so that in addition to using the toilet, user can quickly and easily learn their ECG data to understand their heart health condition, so as to detect and deal with possible diseases as soon as possible.

2. The electrocardiographic lead monitoring module according to the present invention includes an electrocardiographic lead monitoring probe arranged on the body and an electrical signal processing circuit electrically connected to the electrocardiographic lead monitoring probe. Human body ECG signals are obtained by the electrocardiographic lead probe and transmitted to the electrical signal processing circuit. The processed electrical signals are transmitted to the controller by the electrical signal processing circuit. The processed electrical signals transmitted to the controller are further processed to obtain electrocardiographic lead data. The display or voice prompt module is controlled to output the data. The electrocardiographic lead monitoring module has the features of simple structure and low cost.

3. As a further improvement of the present invention, the body 1 according to the present invention is provided with armrest 11. Three electrocardiographic lead monitoring probes 41 are respectively arranged on the toilet seat and the armrest, and used for receiving the ECG signals from the human legs and the human hands. According to the present invention, preferably, a three-lead ECG data acquisition method is used. The electrocardiographic lead monitoring probes are arranged on the toilet seat and the armrest. When the user sits down and uses the toilet, the user naturally contacts the electrocardiographic lead monitoring probes, so that the collection of the ECG data is more convenient.

4. As a further improvement of the present invention, the present invention further includes a human body sensing module that is electrically connected to the controller to sense whether the human body has sat down. When the user sits on the toilet of the present invention, the controller learns that the user has sat down, on the toilet of the present invention, through the human body sensing module, so that the electrocardiographic lead monitoring module can be started to collect and output the electrocardiographic lead data. The configuration of the human body sensing module can facilitate the intelligent control of the present invention and make the collection and output of the electrocardiographic lead data more convenient. When the user leaves, the modules that are not used can automatically enter dormancy, such that the present invention has the advantage of saving energy.

DETAILED DESCRIPTION OF THE INVENTION

Figure 1:
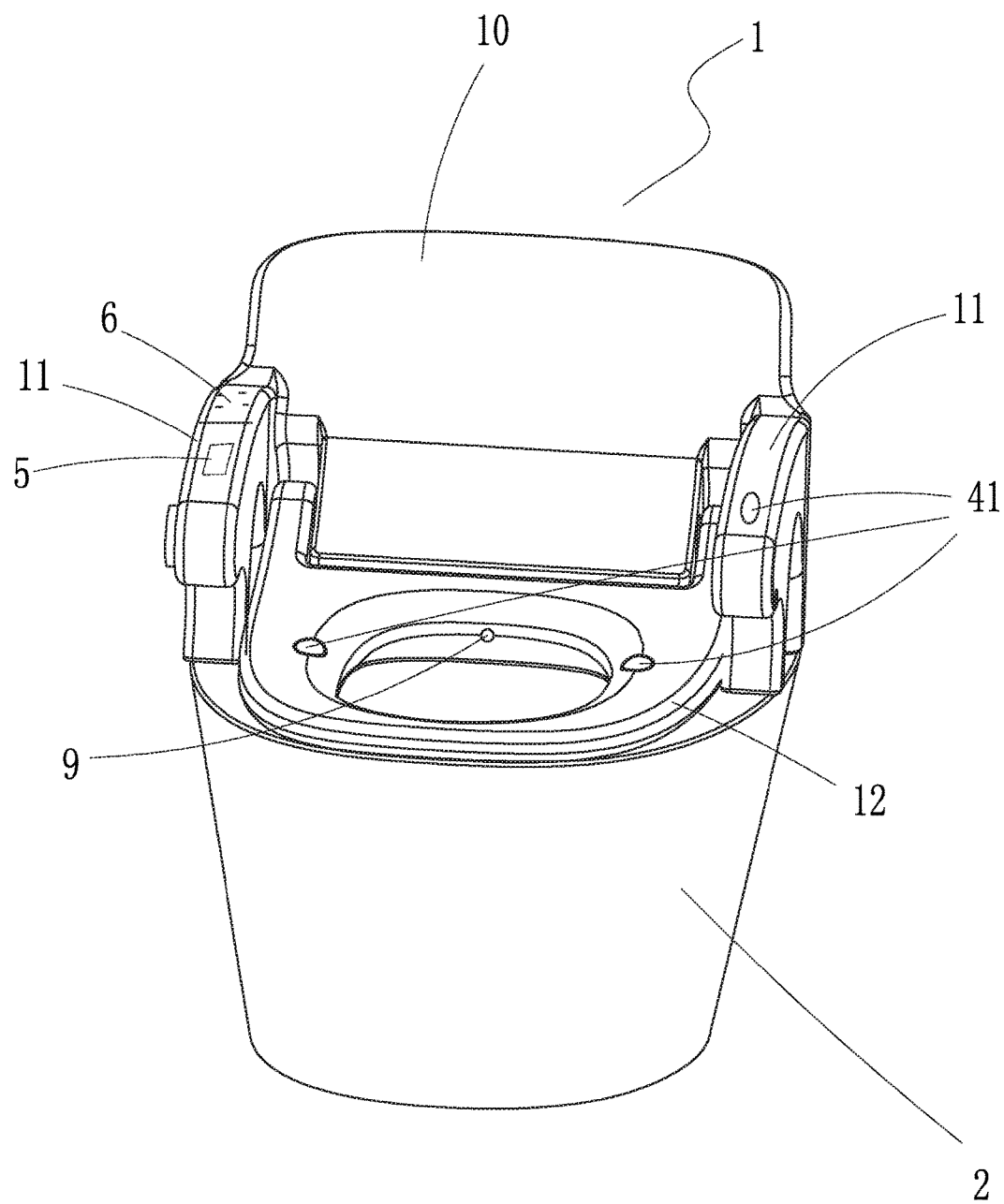
FIG. 1 is a perspective view of the present invention.
Figure 2:
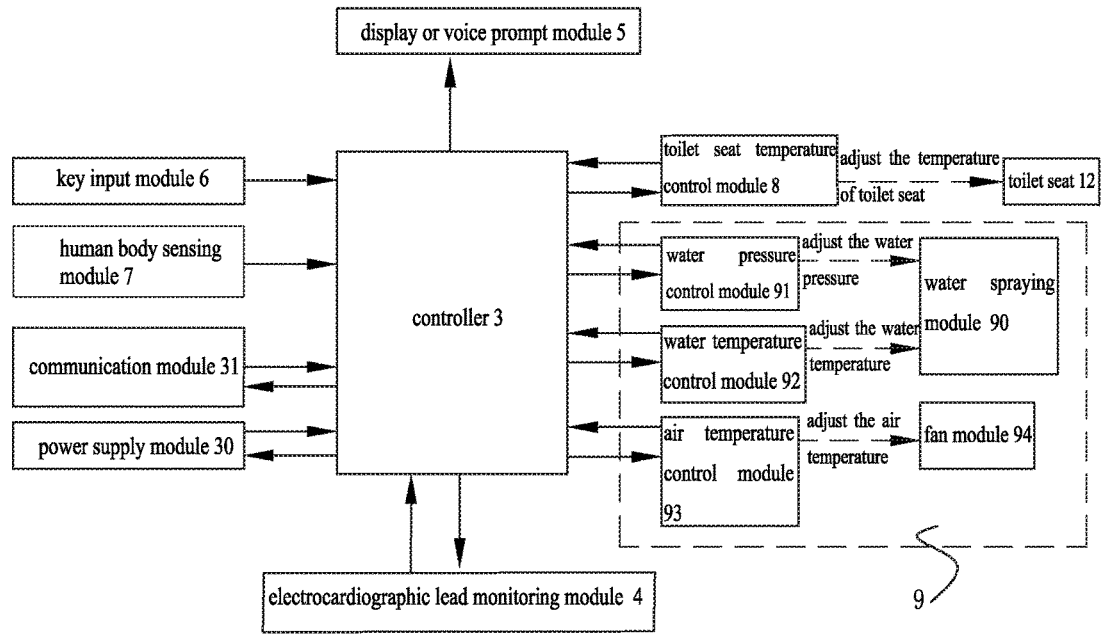
FIG. 2 is a structural block diagram of the system of the present invention.
Figure 3:
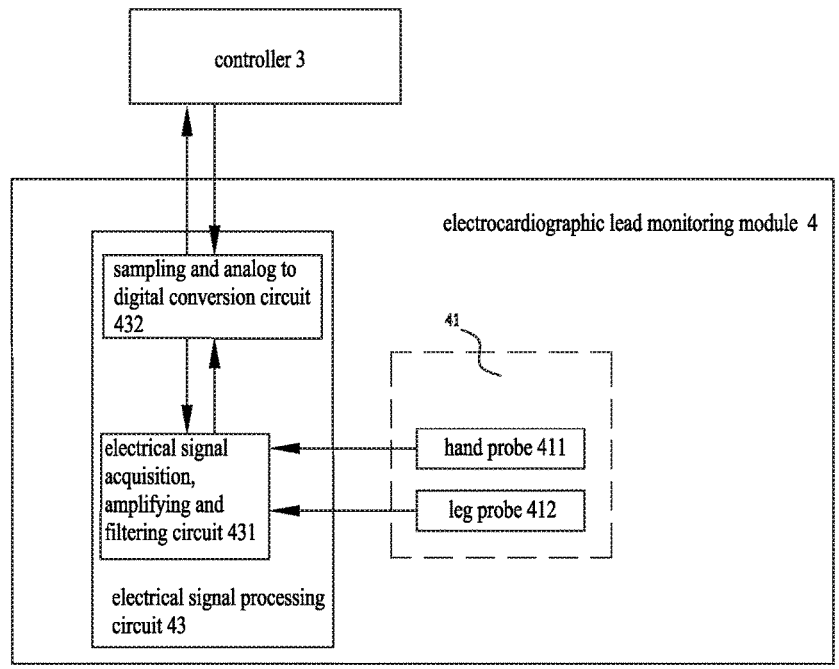
FIG. 3 is a constitution diagram of the electrocardiographic lead monitoring module of the present invention.
Figure 4:
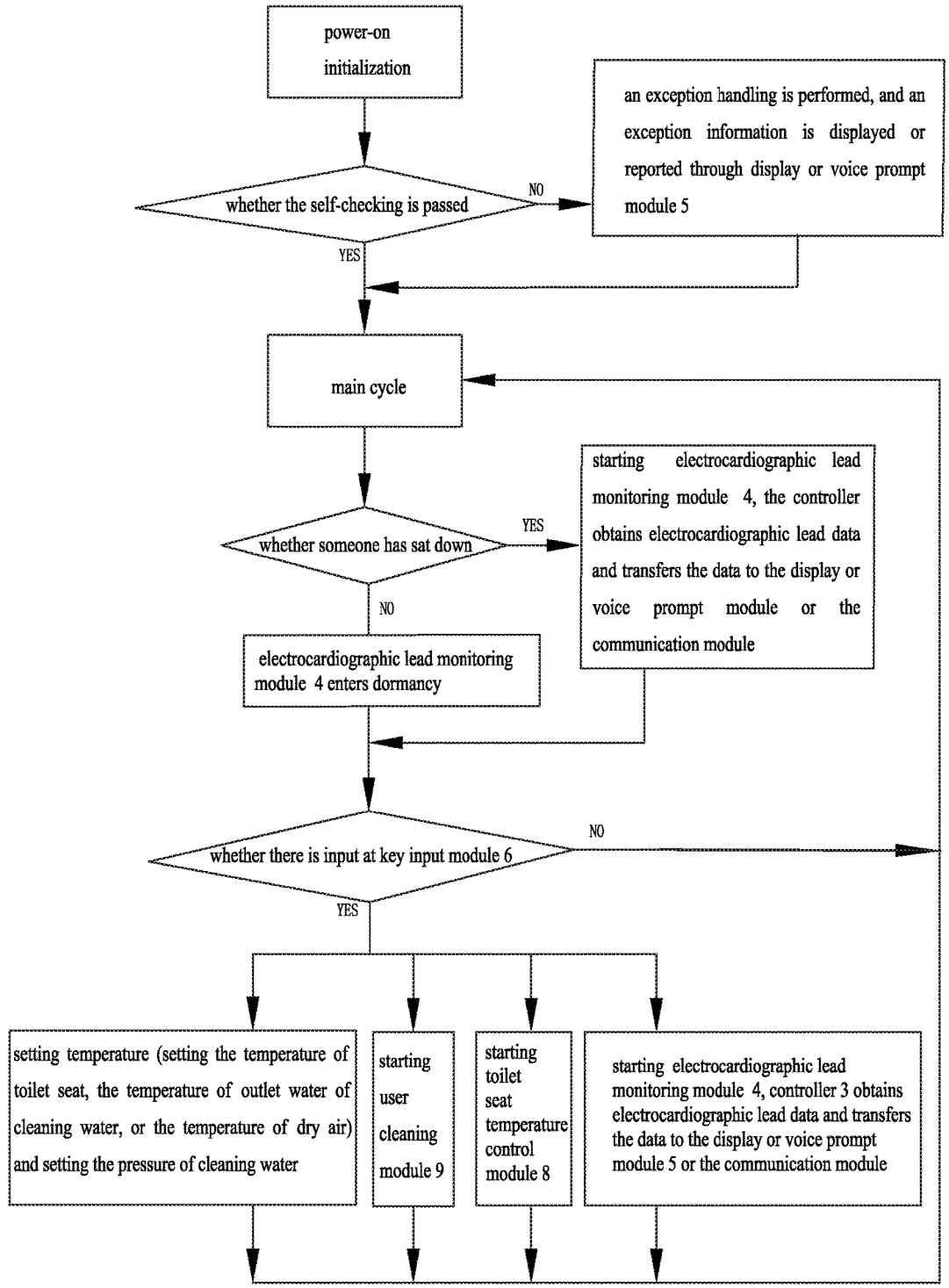
FIG. 4 is a control flowchart of the present invention.

The specific embodiments of the present invention will be further described in detail hereinafter with reference to FIGS. 1 to 4.

A smart toilet with a function of electrocardiographic lead monitoring including toilet base 2, body 1 connected to the toilet base. Body 1 is provided with controller 3 and electrocardiographic lead monitoring module 4, display or voice prompt module 5, and power supply module 30 for supplying power, wherein electrocardiographic lead monitoring module 4, display or voice prompt module 5, and power supply module 30 are electrically connected to controller 3, respectively. Electrocardiographic lead monitoring module 4 further includes electrocardiographic lead monitoring probes 41 arranged on the body and electrical signal processing circuit 43 electrically connected to electrocardiographic lead monitoring probes 41. Human body ECG signals are obtained by electrocardiographic lead probes 41 and transmitted to electrical signal processing circuit 43. The processed electrical signals are transmitted to the controller by electrical signal processing circuit 43. The processed electrical signal transmitted to the controller is further processed to obtain human body electrocardiographic lead data. Display or voice prompt module 5 is controlled to output the data. The electrical signals refer to current signals or voltage signals.

After a person sits down on the toilet of the present invention, the electrocardiographic lead monitoring probes in the electrocardiographic lead monitoring module contact with the human body to obtain human body ECG signals. The ECG signals are transmitted to the controller after acquisition, amplification, filtering, sampling and performing analog-to-digital conversion in the electrical signal processing circuit of the electrocardiographic lead monitoring module. The obtained data is processed by the controller to obtain the electrocardiographic lead data, and the electrocardiographic data is output by the display or voice prompt module. Electrical signal processing circuit 43 includes electrical signal acquisition, amplifying and filtering circuit 431, sampling and analog to digital conversion circuit 432. Certainly, electrical signal processing circuit 43 can also be provided inside controller 3.

In addition to the general ECG data, the electrocardiogram lead data may further include parameters such as heart rate and heart rhythm, and the controller can also obtain the contents of health assessment and diet workout suggestions according to the above data, and output the above data or contents through the display or voice prompt module.

In order to facilitate operations of the present invention, body 1 is further provided with key input module 6 electrically connected to controller 3 and used for sending operation information of the user back to controller 3.

In order to facilitate replacement, cleaning, and sitting-down of the user, body 1 includes main body 10, and toilet seat 12 pivotally connected to main body 10, wherein after being rotated, the toilet seat covers toilet base 2 main body 10 can also be used as a backrest to make the user more comfortable when sitting on toilet base 2.

In order to facilitate the user to get up, body 1 comprises main body 10 and armrest 11 arranged on main body 10. In order to facilitate the operations of the present invention, display or voice prompt module 5 and the key input module 6 are preferably disposed on armrest 11.

The present invention preferably uses the three-lead form of electrocardiographic lead monitoring: The electrocardiographic lead monitoring probe 41 includes hand probe 411 and leg probe 412. There are three electrocardiographic lead monitoring probes 41 respectively arranged on the toilet seat and the armrest to receive ECG signals from the human legs and the human hand. As a preferable solution, two electrocardiographic lead monitoring probes are arranged on the toilet seat, and one electrocardiographic lead monitoring probe is arranged on the armrest. When the user sits on the toilet seat, skin of both legs contacts with the electrocardiographic lead monitoring probes on the toilet seat of the toilet, and then user's hand is put on the armrest of the toilet and contacts with the electrocardiographic lead monitoring probe on the armrest. At this moment, the legs and hand of the user and three electrocardiographic lead monitoring probes form a three-lead impedance circuit R, F, AVR. The three-lead electrocardiographic signals are filtered, amplified, sampled and AD converted in electrical signal processing circuit 43, and then are transmitted to the controller. The controller processes the received signals to obtain the electrocardiographic lead data. Finally, the controller outputs the electrocardiographic lead data through display or voice prompt module. As another preferred solution, we can also provide two electrocardiographic monitoring probes on the armrests and another electrocardiographic monitoring probe on the toilet seat.

In order to facilitate intelligent control, the smart toilet further comprises human body sensing module 7 which is electrically connected to controller 3 and is used to sense whether the human body has sat down. "Sitting down" refers to the user sitting on the toilet base or toilet seat.

Preferably, human body sensing module 7 includes a capacitive sensor or a pressure sensor or an inductive electrode plate electrically connected to controller 3 and used to sense whether the user has sat down. The capacitive sensor, the pressure sensor, or the inductive electrode plate is arranged on toilet base 2 or body 1. When the person has sat down, the capacitive sensor, the pressure sensor, or the inductive electrode plate directly or indirectly contacts human body, causing the capacitance change of the capacitive sensor, making the pressure sensor generate the piezoelectric effects, or leading to the current change or voltage change of the circuit connected to the sensor or inductive electrode plate. The electrical parameters, the electrical signals, or changes of the current and voltage can be identified by the controller. Therefore, the controller can determine whether the user has sat down.

Human body sensing module 7 uses a capacitive sensor, a pressure sensor, or an inductive electrode plate to sense whether the human body has sat down or not. Of course, the human body sensing module may also sense whether the human body has sat down by the following methods. An infrared detection sensor is used to detect the infrared rays sent from the human body, to sense whether the human body has sat down; the properties of the human bio-electricity or human body conduction are utilized to detect whether the human body has sat down. All the above situations belong to the category of human body sensing detection module and should fall within the protection scope of the present invention.

In order to enrich functions, the smart toilet further comprises toilet seat temperature controlling module 8 electrically connected to the controller 3 and used for controlling the temperature of the toilet seat, wherein toilet seat temperature controlling module 8 comprises a temperature sensor and a toilet seat heating module, which are arranged on the toilet seat and respectively electrically connected to the controller. The toilet seat heating module can include an electric heating tube or electric heating wire or electromagnetic heating group, and further includes some necessary power and control circuits. The user can easily adjust the temperature of the toilet seat through toilet seat temperature control module 8, which is beneficial for enhancing the user experience of the present invention.

The user can set the temperature of the toilet seat through the controller and the key input module 6. When the temperature sensor detects that the temperature of the toilet seat has not reached the predetermined temperature, the controller controls the toilet seat heating module to heat the toilet seat. When the temperature sensor detects that the temperature of the toilet seat exceeds the predetermined temperature, the controller controls the heating module of the toilet seat to stop heating. The temperature of the toilet seat is stabilized by the above operations at the set temperature.

In order to enrich the functions, the smart toilet further comprises user cleaning module 9 electrically connected to controller 3, and user cleaning module 9 includes water spraying module 90 for providing cleaning water, water pressure control module 91 for controlling the water pressure of the cleaning water, water temperature control module 92 for controlling the water temperature of the cleaning water, fan module 94 for providing drying air and air temperature control module 93 for controlling the temperature of the drying air. Water pressure control module 91, water temperature control module 92, and air temperature control module 93 are electrically connected to controller 3. After using the toilet, the controller is notified by the key input module to start user cleaning module 9, and the user cleaning module cleans and dries the user according to the water temperature, the water pressure and the drying air temperature set by the user. The cleaning includes the hip cleaning and the female cleaning. The cleaning water is provided by the water spraying module. The water spraying module is controlled by the water temperature control module 92 and the water pressure control module 91. Users can set the water pressure and the cleaning water temperature through the controller. The drying air is provided by the fan module, which is controlled by the air temperature control module, and the user can set the temperature of the drying air through the controller.

The water spraying module 90 includes a nozzle for water outlet and a water pipe connecting the nozzle to external water source. The water temperature control module 92 includes the temperature sensor and the cleaning water heating module, that are provided on the water pipe and are electrically connected to controller 3 respectively. The water pressure control module 91 includes a proportional valve which is provided between the nozzle and the water pipe and is electrically connected to the controller. The air temperature control module includes a temperature sensor and a drying air heating module that are electrically connected to the controller respectively. The user can set the water temperature and the water pressure of the outlet water of the cleaning water through the controller and the key input module. The controller heats up the cleaning water in the water pipe based on the set water temperature of the cleaning water. The temperature sensor senses the temperature of the cleaning water in the water pipe. If the temperature is lower than the set temperature, cleaning water heating module is started to heat up the cleaning water. If the temperature is higher than the set temperature, the cleaning water heating module is turned off. Thus, the temperature of the outlet water of the cleaning water is kept constant. A proportional valve is provided between the nozzle and the water pipe. The proportional valve is electrically connected to the controller and is controlled by the controller. The controller adjusts an opening degree of the proportional valve based on the set water pressure of the outlet water of the cleaning water, so as to adjust the water pressure of the outlet water of the cleaning water. In addition, the user can also set the temperature of the drying air through the controller. The air temperature control module includes the temperature sensor and the drying air heating module that are electrically connected to the controller respectively. When the temperature of the drying air is lower than the set temperature of drying air, the drying air heating module is started, so as to heat up the drying air. When the temperature of drying air is higher than the set temperature, the heating of drying air is stopped. With the above method, the air temperature control module keeps the temperature of drying air at the set temperature. The drying air heating module and cleaning water heating module can be heating wire, heating rod, electromagnetic heating group, along with corresponding power supply circuit and control circuit.

The smart toilet further includes communication module 31 which is electrically connected to the controller. The communication module 31 communicates with a smart device. The electrocardiographic lead data of the human body are transferred through communication module 31 to the smart device and is displayed thereon. The smart device can be a cellphone, a computer, and so on. The communication module communicates with the smart device. The communicating methods can be WIFI, infrared communication, NFC near field communication, and so on. The smart device such as the cellphone can display the electrocardiographic lead data of the human body with an APP. Certainly, the smart device can also control the present invention through the communication module.

A control method of a smart toilet with a function of electrocardiographic lead monitoring, wherein the method includes the following steps:

A: Power-on and initialization: an initial state of each connected module is initialized through controller 3.

B: Execution of power-on self-checking: fault detection is conducted by controller 3 on each module. If the self-checking is passed, the procedure proceeds to step C. Otherwise, an exception handling is performed, and exception information is displayed or reported through display or voice prompt module 5. The fault detection includes detecting the circuit of each module and the controller circuit for short circuit, disconnection, or current/voltage overload.

C: Entering a main cycle, controller 3 detects whether someone has sat down through human body sensing module 7. If someone has sat down, electrocardiographic lead monitoring module 4 is started by controller 3; transmitting human body ECG signals obtained by electrocardiographic lead monitoring module 4 to the controller; processing the electrical signals received by the controller to obtain human body electrocardiographic lead data; controlling display or voice prompt module 5 or communication module 31 communicating with the smart device to output the human body electrocardiographic lead data, then proceeding to step D; if no user has sat down, controlling electrocardiographic lead monitoring module 4 by controller 3 to enter dormancy, and then proceeding to step D; the dormancy is referred that the controller stops to receive the electrical signal transmitted from the electrocardiographic lead monitoring module; starting the electrocardiographic lead monitoring module is referred that the controller begins to receive the electrical signal transmitted from the electrocardiographic lead monitoring module.

D: Controller 3 detects whether there is an input at key input module 6. If there is no input, the procedure returns to step C. If there is an input, the procedure proceeds to step E.

E: Controller 3 performs corresponding operations based on the input at key input module 6, for example, setting the temperature of the cleaning water, the water pressure of the outlet water of the cleaning water, and the temperature of drying air; starting user cleaning module 9 to provide the cleaning water or the drying air.

The smart toilet includes toilet base 2. The smart toilet further includes body 1 which is connected to the toilet base. The body 1 is provided with controller 3 and following modules that are electrically connected to controller 3 respectively, i.e., electrocardiographic lead monitoring module 4, display or voice prompt module 5, and power supply module 30 which is used to provide power. Electrocardiographic lead monitoring module 4 includes electrocardiographic lead monitoring probe 41 arranged on the body and electrical signal processing circuit 43 electrically connected to electrocardiographic lead monitoring probes 41. Human body ECG signals are obtained by electrocardiographic lead monitoring probes 41 and transmitted to electrical signal processing circuit 43. The processed electrical signals are transmitted to the controller by electrical signal processing circuit 43. The electrical signals received by the controller are processed to obtain the human body electrocardiographic lead data, and the controller controls display or voice prompt module 5 to output the data.

The smart toilet further includes human body sensing module 7 which is electrically connected to the controller 3 and is used to sense whether the human body has sat down.

The smart toilet further includes user cleaning module 9 which is electrically connected to controller 3. The user cleaning module 9 includes water spraying module 90 which provides cleaning water, water pressure control module 91 which controls the pressure of the cleaning water, water temperature control module 92 which controls the temperature of the cleaning water, fan module 94 which provides the drying air, and air temperature control module 93 which controls the temperature of drying air. The water pressure control module 91, water temperature control module 92, and air temperature control module 93 are electrically connected to controller 3.

The body 1 includes main body 10, and toilet seat 12 which is pivotally connected to main body 10, wherein after being rotated, toilet seat 12 covers toilet base 2. The smart toilet further includes the toilet seat temperature control module 8 which is electrically connected to controller 3 and controls the temperature of the toilet seat. The toilet seat temperature control module 8 includes a temperature sensor and a toilet seat heating module that are provided on the toilet seat and are electrically connected to the controller respectively. Step E further includes performing corresponding operations based on the input at key input module 6: setting the temperature of the toilet seat, and starting the toilet seat temperature control module to adjust the temperature of the toilet seat.

Step E further includes performing corresponding operations based on the input at key input module 6. More specifically, controller 3 starts electrocardiographic lead monitoring module 4. Electrocardiographic lead monitoring module 4 obtains human body ECG signals, which are transferred to the controller. The controller processes the obtained electrical signals to obtain the electrocardiographic lead data of the human body and controls the display or voice prompt module 5 or communicate module 31 which communicates with the smart device to output the electrocardiographic lead data.

The human body sensing module 7 includes a capacitive sensor, a pressure sensor, or an inductive electrode plate which is electrically connected to controller 3 and is used to sense whether the user has sat down. The capacitive sensor, the pressure sensor, or the inductive electrode plate is provided on the toilet base 2 or body 1. After the person sits down, the person directly or indirectly contacts the capacitive sensor, the pressure sensor, or the inductive electrode plate, causing the capacitance change of the capacitive sensor, making the pressure sensor generate the piezoelectric effects, or leading to the current change or voltage change of the circuit connected to the sensor or inductive electrode plate. The electrical parameters, the electrical signals, or changes of the current and voltage can be identified by the controller. Therefore, the controller can determine whether the user has sat down. The term "sit down" refers to that the user sits down on the toilet base or the toilet seat.

What is claimed is:

1. A smart toilet with a function of electrocardiographic lead monitoring, comprising: a toilet base and a body connected to the toilet base; wherein, the body is provided with a controller, an electrocardiographic lead monitoring module, a display or voice prompt module, and a power supply module for supplying power, wherein the electrocardiographic lead monitoring module, the display or voice prompt module, and the power supply module are electrically connected to the controller respectively;

wherein the electrocardiographic lead monitoring module further includes an electrocardiographic lead monitoring probe arranged on the body and an electrical signal processing circuit electrically connected to the electrocardiographic lead monitoring probe;

wherein, a human body ECG signal is obtained by the electrocardiographic lead probe and transmitted to the electrical signal processing circuit, a processed electrical signal is transmitted to the controller by the electrical signal processing circuit, the processed electrical signal transmitted to the controller is further processed to obtain a human body electrocardiographic lead data, and the display or voice prompt module is controlled by the controller to output the data;

the body includes a main body and an armrest arranged on the main body; and two electrocardiographic lead monitoring probes are arranged on the toilet seat to contact with a right leg and a left leg respectively, and one electrocardiographic lead monitoring probe is arranged on the armrest to form a three-lead impedance circuit for receiving ECG signals from human legs and human hand.

2. The smart toilet with a function of electrocardiographic lead monitoring of claim 1, wherein the body is further provided with a key input module electrically connected to the controller, wherein the key input module is used to send operation information of a user back to the controller.

3. The smart toilet with a function of electrocardiographic lead monitoring of claim 2, wherein the smart toilet further comprises a user cleaning module electrically connected to the controller; the user cleaning module includes a water spraying module configured to provide cleaning water, a water pressure control module configured to control an outlet water pressure of the cleaning water, a water temperature control module configured to control an outlet water temperature of the cleaning water, a fan module configured to provide drying air and an air temperature control module configured to control the temperature of the drying air; the water pressure control module, the water temperature control module and the air temperature control module are electrically connected to the controller.

4. The smart toilet with a function of electrocardiographic lead monitoring of claim 3, wherein the water spraying module comprises a nozzle for outlet water and a water pipe connecting the nozzle and an external water source; the water temperature control module comprises a second temperature sensor and a cleaning water heating module, wherein the second temperature sensor and the cleaning water heating module are arranged on the water pipe and electrically connected to the controller respectively;

the water pressure control module comprises a proportional valve arranged between the nozzle and the water pipe and electrically connected to the controller; the air temperature control module comprises a third temperature sensor and a drying air heating module electrically connected to the controller.

5. The smart toilet with a function of electrocardiographic lead monitoring of claim 1, wherein the body comprises a main body and a toilet seat pivotally connected to the main body, wherein after being rotated, the toilet seat covers the toilet base.

6. The smart toilet with a function of electrocardiographic lead monitoring of claim 5, wherein the smart toilet further comprises a toilet seat temperature control module electrically connected to the controller and used to control temperature of the toilet seat; wherein, the toilet seat temperature control module includes a first temperature sensor and a toilet seat heating module arranged on the toilet seat and electrically connected to the controller.

7. The smart toilet with a function of electrocardiographic lead monitoring of claim 5, wherein the smart toilet further comprises a human body sensing module electrically connected to the controller to sense whether the human body has sat down.

8. The smart toilet with a function of electrocardiographic lead monitoring of claim 1, wherein the smart toilet further comprises a human body sensing module electrically connected to the controller to sense whether the human body has sat down.

9. The smart toilet with a function of electrocardiographic lead monitoring of claim 8, wherein the human body sensing module comprises a capacitive sensor or a pressure sensor or an inductive electrode plate electrically connected to the controller and is used to sense whether the user has sat down, and the capacitive sensor or the pressure sensor or the inductive electrode plate is arranged on the toilet base or the body.

10. The smart toilet with a function of electrocardiographic lead monitoring of claim 1, wherein the smart toilet further comprises a communication module electrically connected to the controller; wherein the communication module communicates with a smart device; the electrocardiographic lead data is transmitted to and displayed on the smart device through the communication module.

11. A control method for a smart toilet with a function of electrocardiographic lead monitoring, comprising:

step A, initializing an initial state of each connection module through a controller;

step B, performing a fault detection for each module through a controller, if the self-checking is passed, proceeding to step C, otherwise, conducting an exception handling, displaying or reporting exception information through a display or voice prompt module;

step C, entering into a main cycle and detecting whether user has sat down on the toilet by the controller through a human body sensing module; if a user has sat down, starting an electrocardiographic lead monitoring module by the controller; obtaining a human body ECG signal by the electrocardiographic lead monitoring module and transmitting the a human body ECG signal to the controller; processing the electrical signal received by the controller to obtain electrocardiographic lead data of the human body; controlling the display or voice prompt module or a communication module communicating with a smart device to output the electrocardiographic lead data of the human body, then proceeding to step D; if no user has sat down, controlling the electrocardiographic lead monitoring module by the controller to enter dormancy, and then proceeding to step D;

step D, detecting whether there is an input from a key input module by the controller; if there is no input, returning to the step C, otherwise proceeding to step E;

step E, perform corresponding operations by the controller according to the input at the key input module: setting an outlet water temperature for cleaning water, setting outlet water pressure for the cleaning water, and setting drying air temperature; and starting a user cleaning module to provide the cleaning water or the drying air;

wherein the smart toilet includes a toilet base and a body connected to the toilet base; the body is provided with a controller and an electrocardiographic lead monitoring module, a display or voice prompt module, a power supply module for supplying power, wherein the electrocardiographic lead monitoring module, the display or voice prompt module and the power supply module are electrically connected to the controller respectively;

wherein the electrocardiographic lead monitoring module includes an electrocardiographic lead monitoring probe arranged on the body and an electrical signal processing circuit electrically connected to the electrocardiographic lead monitoring probe; a human body ECG signal is obtained by the electrocardiographic lead monitoring probe and transmitted to the electrical signal processing circuit; the processed electrical signal is transmitted to the controller by the electrical signal processing circuit; the electrical signal received by the controller is processed to obtain the human body electrocardiographic lead data, and the display or voice prompt module is controlled to output the data;

the smart toilet further includes a human body sensing module electrically connected to the controller and used to sense whether the human body has sat down;

the smart toilet further includes the user cleaning module electrically connected to the controller; the user cleaning module includes a water spraying module for providing cleaning water, a water pressure control module for controlling outlet water pressure of the cleaning water, a water temperature control module for controlling an outlet water temperature of the cleaning water, a fan module for providing drying air and an air temperature control module for controlling the temperature of the drying air; the water pressure control module, the water temperature control module and the air temperature control module are electrically connected to the controller;

the body comprises a main body and an armrest arranged on the main body; and two electrocardiographic lead monitoring probes are arranged on the toilet seat to contact with a right leg and a left leg respectively, and one electrocardiographic lead monitoring probe is arranged on the armrest to form a three-lead impedance circuit for receiving ECG signals from human leg and human hand.

12. The control method for the smart toilet with a function of electrocardiographic lead monitoring of claim 11, wherein the toilet seat is pivotally connected to the main body, after being rotated, the toilet seat covers the toilet base;

the smart toilet further comprises a toilet seat temperature control module electrically connected to the controller to control the temperature of the toilet seat; the toilet seat temperature control module includes a first temperature sensor and a toilet seat heating module arranged on the toilet seat and electrically connected to the controller respectively;

the step E further includes performing corresponding operations by the controller according to the input at the key input module: setting the temperature of the toilet seat, and starting the toilet seat temperature control module to adjust the temperature of the toilet seat.

13. The control method for the smart toilet with a function of electrocardiographic lead monitoring of claim 11, wherein the step E further comprises performing the corresponding operations by the controller according to the input at the key input module: starting the electrocardiographic lead monitoring module by the controller; obtaining an human body ECG signal by the electrocardiographic lead monitoring module; transmitting the human body ECG signal to the controller; processing the electrical signal received by the controller to obtain the human body electrocardiographic lead data; and controlling the display or voice prompt module or the communication module communicating with the smart device to output the human body electrocardiographic lead data.

14. The control method for the smart toilet with a function of electrocardiographic lead monitoring of claim 11, wherein the human body sensing module comprises a capacitive sensor or a pressure sensor or an inductive electrode plate electrically connected to the controller to sense whether the user has sat down; and the capacitive sensor or the pressure sensor or the inductive electrode plate is arranged on the toilet base or the body.

* * * * *